(12) United States Patent
Neidert et al.

(10) Patent No.: US 8,204,574 B2
(45) Date of Patent: Jun. 19, 2012

(54) STYLET FOR USE WITH IMAGE GUIDED SYSTEMS

(75) Inventors: Michael R. Neidert, County Galway (IE); Ian Matheson, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 880 days.

(21) Appl. No.: 12/275,377

(22) Filed: Nov. 21, 2008

(65) Prior Publication Data
US 2010/0130851 A1    May 27, 2010

(51) Int. Cl.
*A61B 5/05* (2006.01)
(52) U.S. Cl. .................. 600/423; 600/422; 600/410
(58) Field of Classification Search .......... 600/407–429, 600/114, 118, 300, 317; 604/49–53, 508–522
See application file for complete search history.

(56) References Cited

U.S. PATENT DOCUMENTS

| | | | |
|---|---|---|---|
| 4,601,713 A | | 7/1986 | Fuqua |
| 4,681,564 A | | 7/1987 | Landreneau |
| 4,710,181 A | | 12/1987 | Fuqua |
| 5,106,368 A | | 4/1992 | Uldall et al. |
| 5,226,887 A | | 7/1993 | Farr et al. |
| 5,324,269 A | | 6/1994 | Miraki |
| 5,443,492 A | * | 8/1995 | Stokes et al. ............... 607/131 |
| 5,575,814 A | * | 11/1996 | Giele et al. ................. 607/127 |
| 5,618,267 A | | 4/1997 | Palestrant |
| 5,674,272 A | * | 10/1997 | Bush et al. ................. 607/122 |
| 5,776,096 A | | 7/1998 | Fields |
| 5,827,243 A | | 10/1998 | Palestrant |
| 6,235,038 B1 | | 5/2001 | Hunter et al. |
| 6,527,790 B2 | | 3/2003 | Chien et al. |
| 6,689,125 B1 | * | 2/2004 | Keith et al. ................. 606/32 |
| 6,992,477 B2 | | 1/2006 | Govari |
| 6,995,729 B2 | | 2/2006 | Govari et al. |
| 7,176,846 B2 | | 2/2007 | Mejia et al. |
| 7,366,562 B2 | | 4/2008 | Dukesherer et al. |
| 7,881,769 B2 | * | 2/2011 | Sobe ........................... 600/424 |
| 2004/0097804 A1 | * | 5/2004 | Sobe ........................... 600/424 |
| 2005/0283067 A1 | | 12/2005 | Sobe |
| 2007/0043413 A1 | | 2/2007 | Eversull et al. |
| 2008/0033502 A1 | * | 2/2008 | Harris et al. ............... 607/45 |
| 2008/0255446 A1 | * | 10/2008 | Akins ......................... 600/424 |

(Continued)

FOREIGN PATENT DOCUMENTS

| EP | 1510182 | 3/2005 |
|---|---|---|
| EP | 1743591 | 1/2007 |

OTHER PUBLICATIONS (PCT/US2009/064955) PCT Notification of Transmittal of the International Search Report and the Written Opinion of the International Searching Authority, 11 pages.

(Continued)

*Primary Examiner* — Sanjay Cattungal

(57) ABSTRACT

A stylet for an image guided system, which includes a locating device and which is operable for emitting an electromagnetic field for locating the stylet. The stylet includes a flexible elongate member, an electrically conductive member, and a reinforcement member. The reinforcement member is disposed inside the electrically conductive member and is made out of a magnetic material. The reinforcement member reinforces the stylet and provides electrical communication between the conductive member and the locating device such that current induced in the conductive member is transmitted to the locating device via the reinforcement member.

16 Claims, 4 Drawing Sheets

U.S. PATENT DOCUMENTS

| | | | | |
|---|---|---|---|---|
| 2008/0319376 A1* | 12/2008 | Wilcox et al. | ............... | 604/22 |
| 2010/0125219 A1* | 5/2010 | Harris et al. | ............... | 600/544 |
| 2010/0324644 A1* | 12/2010 | Levi et al. | ............... | 607/133 |
| 2011/0130655 A1* | 6/2011 | Nielson et al. | ............... | 600/426 |
| 2011/0166430 A1* | 7/2011 | Harris et al. | ............... | 600/301 |
| 2011/0202137 A1* | 8/2011 | Keith et al. | ............... | 623/17.16 |

OTHER PUBLICATIONS

Medtronic Navigation Tracking Technologies webpage; StealthStation® AXIEM™ System (www.medtronicnavigation.com/procedures/navigation/tracking.jsp).

* cited by examiner

STYLET FOR USE WITH IMAGE GUIDED SYSTEMS

FIELD

The present disclosure relates to image guided systems and, more particularly, to a stylet for use with image guided systems.

BACKGROUND

This section provides background information related to the present disclosure which is not necessarily prior art.

Certain medical procedures involve positioning medical devices, such as catheters, stimulation leads, and the like, within a patient. In some cases, medical professionals rely on an image guided system to position these medical devices. For example, these image guided systems include a stylet with a conductive coil that is supported in a known position relative to the medical device. The stylet is coupled to the medical device to be inserted into the patient through a prepared incision, and a varying electromagnetic field is generated about the patient. The field induces a current in the coil that is dependent on the position and vector of the stylet. The current is detected in order to determine the location of the coil and, thus, the location of the medical device within the patient. Moreover, these techniques can be used with an imaging device (e.g., fluoroscopy, magnetic resonance imaging (MRI), computed tomography (CT), etc.) so that the medical professional can see the location of the medical device relative to the patient's anatomy. Thus, the medical device can be positioned with a fair amount of accuracy.

However, conventional stylets may not be practical for certain medical procedures. For instance, conventional stylets may not provide high enough signal-to-noise ratio during use, leading to inaccuracies within the system. More specifically, some stylets are very small in cross sectional area so that they can be routed through small blood vessels and the like, and because of their compact size, the navigation coils provided on these stylets are also small, thereby reducing the signal-to-noise ratio. Also, some stylets are routed through blood vessels or along other non-linear paths, but some conventional stylets may be too rigid to be routed in this manner. Furthermore, medical professionals typically push and twist on one end of the stylet in order to route the stylet along a non-linear path, but some stylets may not adequately transfer these forces longitudinally along the stylet, making the stylet difficult to place in its intended position.

SUMMARY

This section provides a general summary of the disclosure, and is not a comprehensive disclosure of its full scope or all of its features.

A stylet for an image guided system is disclosed. The image guided system includes a locating device and is operable for emitting an electromagnetic field for locating the stylet. The stylet includes a flexible elongate member and an electrically conductive member operatively secured to the flexible elongate member so as to encompass the flexible elongate member. Furthermore, the stylet includes a reinforcement member operatively secured to the flexible elongate member. The reinforcement member is disposed inside the electrically conductive member and is made of a magnetic material. Also, the reinforcement member reinforces the stylet and provides electrical communication between the electrically conductive member and the locating device such that current induced in the electrically conductive member due to the electromagnetic field is transmitted to the locating device via the reinforcement member.

In another aspect, a method for positioning a medical device is disclosed. The method includes electrically connecting an electrically conductive member of a stylet to a locating device via a reinforcement member. The reinforcement member is made of a magnetic material and is disposed inside the electrically conductive member. The method also includes emitting an electromagnetic field relative to the stylet to induce a current in the electrically conductive member. Furthermore, the method includes detecting the current in the electrically conductive member with the locating device to locate the stylet. Moreover, the method includes positioning the medical device relative to the stylet.

In still another aspect, an image guided system is disclosed. The system includes a locating device, a field generator operable for emitting and oscillating an electromagnetic field, and a medical device defining a channel therein. The system further includes a stylet removably disposed within the channel. The stylet includes a reinforcement member having a first member and a second member that are electrically insulated from each other and that are each made out of a magnetic material. A flexible elongate member covers the reinforcement member, and a coil is wound about the flexible elongate member and the reinforcement member. An outer sheath substantially encompasses the coil, the flexible elongate member, and the reinforcement member. The reinforcement member reinforces the stylet. Also, the first member is electrically connected to a positive lead of the coil and locating device, and the second member is electrically connected to a negative lead of the coil and the locating device such that current induced in the coil due to the oscillating electromagnetic field is transmitted to the locating device via the reinforcement member. The locating device is operable to detect the location of the medical device based on the current induced in the coil.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected exemplary embodiments and not all possible implementations, and are not intended to limit the scope of the present disclosure.

Corresponding reference numerals indicate corresponding parts throughout the several views of the drawings.

DETAILED DESCRIPTION

Exemplary embodiments will now be described more fully with reference to the accompanying drawings.

Figure 1:
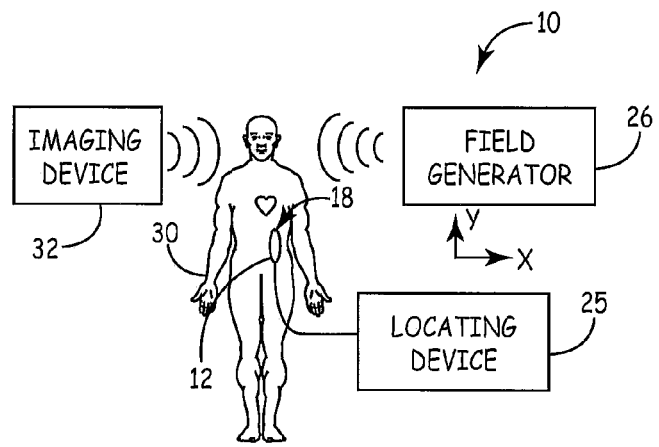
FIG. 1 is a schematic view illustrating an image guiding system according to teachings of the present disclosure.
Figure 2:
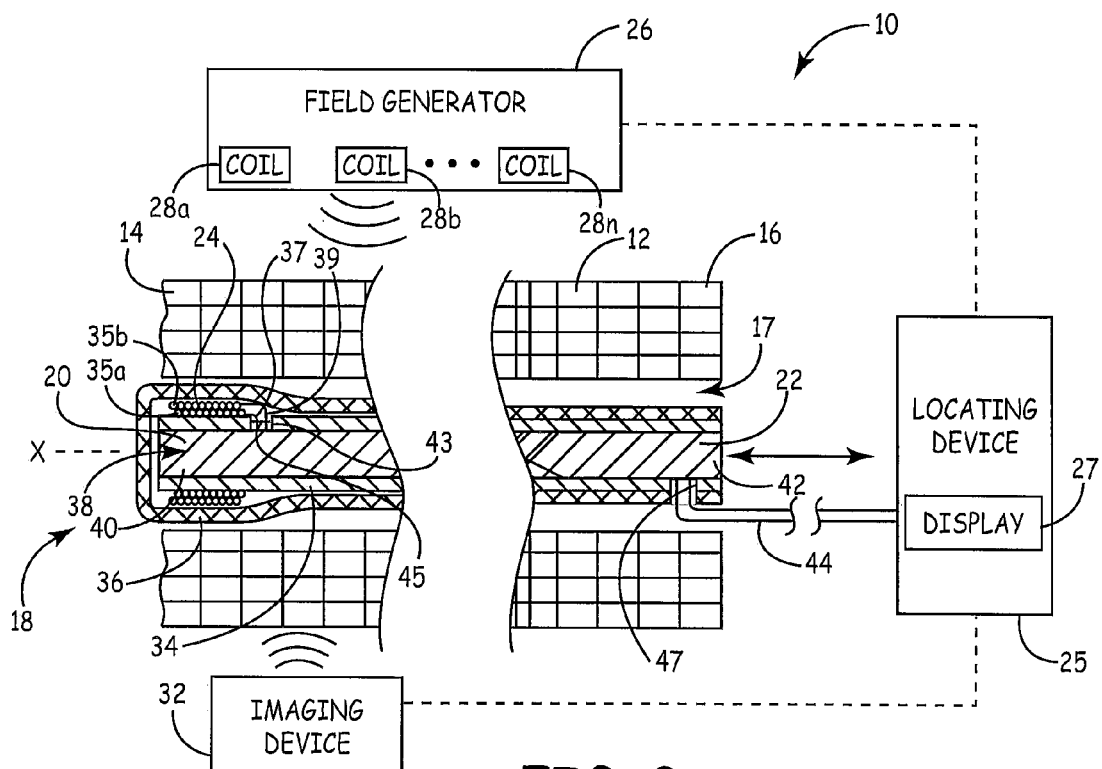
FIG. 2 is a sectional view of a stylet and a medical device for use in the image guided system of FIG. 1.

Referring initially to FIGS. 1 and 2, an image guided system 10 is illustrated schematically. As will be discussed below, the image guided system 10 can be used for the placement of a medical device 12, such as a catheter, a stimulation medical lead, and the like, within a patient. In some exemplary embodiments represented in FIG. 2, the medical device 12 is elongate and tubular and includes a first portion 14 and a second end 16. The first portion 14 can be spaced from the second end 16, and the first portion 14 can be arranged at an opposite end from the second end 16. Furthermore, the medical device 12 can be hollow so as to define a channel 17 extending longitudinally along an axis X thereof. As will be discussed below, the image guided system 10 can be used to locate and position the medical device 12 within the patient 30 (FIG. 1). For instance, the image guided system 10 can be used to position and operatively attach a pacemaker lead in the heart of the patient 30 (e.g. left ventricular lead placement). Moreover, the image guided system 10 can be used in combination with the CARTO XP EP Navigation and Ablation System, which is commercially available from Johnson & Johnson of New Brunswick, N.J. or in combination with the FLUOROMERGE or AXIEM Electromagnetic Tracking systems, which are commercially available from Medtronic, Inc. of Minneapolis, Minn. However, it would be appreciated that the image guided system 10 can be used for the placement of any suitable medical device 12 without departing from the scope of the present disclosure.

Figure 3:
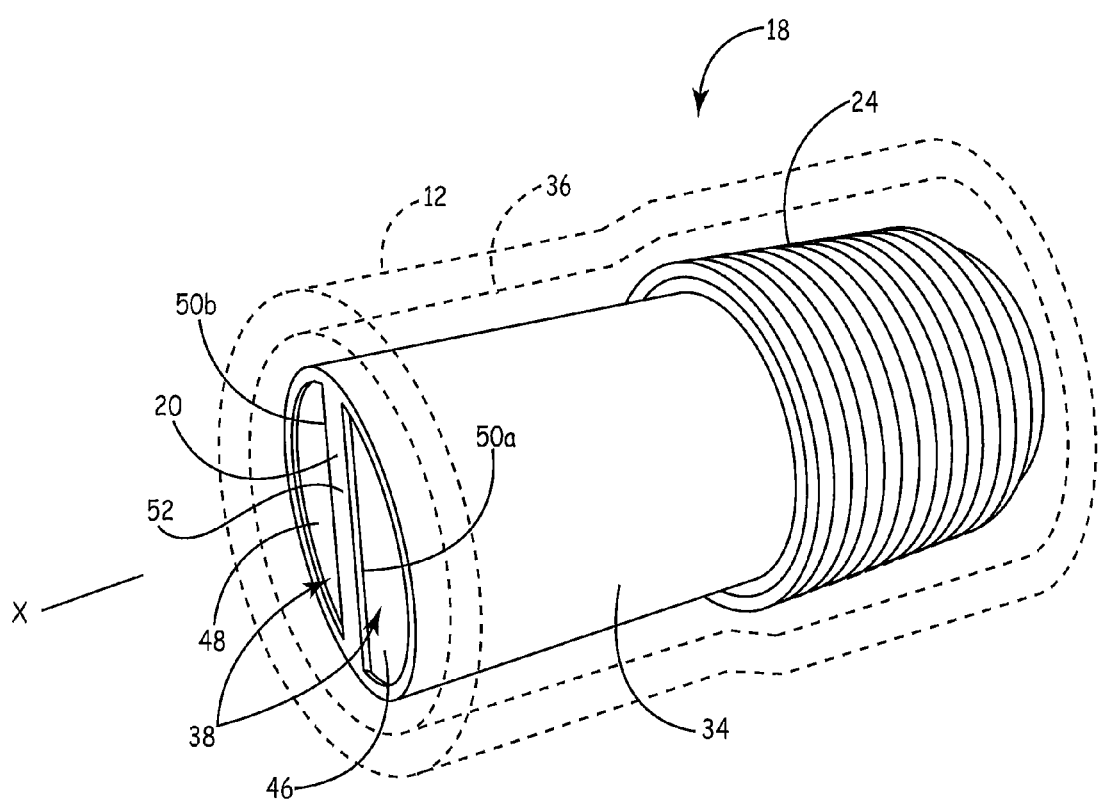
FIG. 3 is a perspective view of the stylet of FIG. 2.

The image guided system 10 can include a stylet 18, such as a stylet 18 according to the exemplary embodiment shown in detail in FIG. 2. As shown, the stylet 18 can be elongate with a first end 20 (i.e., a distal end) and a second end 22 (i.e., a proximal end). As shown in FIG. 3, the stylet 18 can have a generally rounded cross-section (e.g., a circular cross-section). As shown in FIG. 2, the stylet 18 can be removably secured to the medical device 12. For instance, in some exemplary embodiments, the stylet 18 is removably disposed in the channel 17 of the medical device 12 such that the stylet 18 shares the axis X with the medical device.

As shown in FIGS. 2 and 3, the stylet 18 can include a coil 24 adjacent the first end 20. The coil 24 can be made out of any suitable conductive material, such as copper wire that is coated with an insulating material. The coil 24 can be wound helically adjacent the first end 20 of the stylet 18. In some exemplary embodiments, the coil 24 is 50 gauge wire (i.e., 0.001" diameter wire), and in other exemplary embodiments, the coil 24 is made of 52 gauge wire (i.e., 0.0008" diameter wire). Also, the coil 24 can include any suitable length of wire, such as an approximately 0.1" long wire, and the coil 24 can include a plurality of layers as will be discussed. It will be appreciated that the stylet 18 can include any suitable number of coils 24, and it will also be appreciated that the stylet 18 can include any other suitable electrically conductive member in any shape without departing from the scope of the present disclosure.

The coil 24 can be electrically connected to a locating device 25 (FIG. 2). The locating device 25 can be a computer with a microprocessor, memory, and other known computer components, and the locating device 25 can rely on certain algorithms for locating the stylet 18, as will be described in greater detail below. Moreover, the locating device 25 can include a display 27, such as a computer monitor, LCD display, etc., for providing visual feedback relating to the location of the stylet 18, the location of the medical device 12, and/or the anatomy of the patient 30.

Moreover, the image guided system 10 can include a field generator 26 (FIG. 2). The field generator 26 can generate an electromagnetic field about the patient 30. In some exemplary embodiments, the field generator 26 includes a plurality of coils 28a, 28b . . . 28n. It will be appreciated that the field generator 26 can include any suitable number of coils 28a, 28b . . . 28n, each for generating a unique electromagnetic field. In operation, the field generator 26 oscillates as to which coil 28a, 28b . . . 28n is operating, and each of the coils 28a, 28b . . . 28n operates at a different time. Thus, the net electromagnetic field generated by the coils 28a, 28b . . . 28n varies according to which coil 28a, 28b, 28n is operating at any one time.

Accordingly, once the stylet 18 is coupled to the medical device 12 and inserted into the patient 30 through a prepared incision (not shown), the field generator 26 can generate an oscillating electromagnetic field. This field induces a current in the coil 24, and the induced current is transmitted to the locating device 25. The induced current can be dependent on the position and the vector (i.e., the orientation and/or direction of movement) of the stylet 18. Thus, the locating device 25 can triangulate the position of the coil 24 according to known methods relative to the coils 28a, 28b, 28n of the field generator 26. With this data, the locating device 25 can detect the location of the stylet 18. More specifically, in some exemplary embodiments, the locating device 25 can locate the stylet 18 on a Cartesian coordinate system (X, Y, Z) as shown in FIG. 1, and the locating device 25 can also detect the vector (i.e., the orientation and/or direction of movement of the stylet 18). The locating device 25 can locate the stylet 18 on any suitable coordinate system (two-dimensional, three-dimensional, Cartesian, polar, etc.). In some exemplary embodiments, the mechanical properties (e.g., stiffness) of the stylet 18 are known, and the position of the stylet 18 relative to the medical device 12 is known. As such, the locating device 25 can generate an image of the stylet 18 in the medical device 12 on the display 27.

Furthermore, in some exemplary embodiments, the image guided system 10 can include an imaging device 32 for imaging anatomical features of the patient 30. In some exemplary embodiments, the imaging device 32 is a known fluoroscopy (i.e., X-ray) device for generating two-dimensional anatomical images. In other exemplary embodiments, the imaging device 32 is a magnetic resonance imaging (MRI) or computed tomography (CT) device for generating three-dimensional anatomical images. However, it will be appreciated that the imaging device 32 could be of any suitable type. Thus, the imaging device 32 can be used to generate anatomical images of the patient 30, and these anatomical images can be combined with the images of the stylet 18 and medical device 12 generated by the locating device 25. Accordingly, a medical professional can use these images to route the stylet 18 and medical device 12 with a high-degree of precision to an intended position within the patient 30. Once the medical device 12 is in an intended position, the stylet 18 can be removed from the medical device 12 by pulling the stylet 18 out of the channel 17 along the axis X, leaving the medical device 12 in its intended position.

Moreover, the medical professional can use the images to visually detect the amount of slack of the medical device 12 within the patient 30. For instance, if the medical device 12 is a pacemaker lead, the lead is typically placed with enough slack so that, as the heart beats, the lead is unlikely to pull on the ventricular wall or dislodge altogether. Thus, the stylet 18 allows the medical professional to detect the amount of slack before pulling out the stylet 18 from the medical device 12.

The stylet 18 will now be discussed in greater detail with reference to FIGS. 2 and 3. The stylet 18 can include a flexible elongate member 34. In some exemplary embodiments, the flexible elongate member 34 is a hollow tube that is generally flexible to allow the routing of the stylet 18 along a non-linear path. The flexible elongate member 34 can be made out of any suitable material, such as polyimide, for example. As shown in FIGS. 2 and 3, the coil 24 can be operatively secured to the elongate member 34. For instance, in some exemplary embodiments, the coil 24 can wrap around the elongate member 34 such that the coil 24 receives the elongate member 34 therein. In some exemplary embodiments, the coil 24 can include multiple helical layers including a first layer 35a and a second layer 35b. The first layer 35a can be wrapped directly on the elongate member 34, and the second layer 35b can be wrapped on the first layer 35a. It will be appreciated that the coil 24 could include any suitable number of layers 35a, 35b (e.g., two to four). Thus, the multiple layers 35a, 35b can improve the signal-to-noise ratio when current is induced in the coil 24 as described above.

Moreover, in some exemplary embodiments, the first layer 35a includes a lead 37 extending therefrom, and the second layer 35b also includes a lead 39 extending therefrom (FIG. 2). It will be appreciated that the leads 37, 39 have opposite polarities, and the leads 37, 39 enable electrical connection between the coil 24 and the locating device 25, as will be discussed in greater detail.

Moreover, the stylet 18 can include an outer sheath 36 shown in FIG. 2 and shown in phantom in FIG. 3. In some exemplary embodiments, the outer sheath 36 is a hollow tube. The outer sheath 36 can be generally flexible to allow for routing of the stylet 18 along a non-linear path. As shown in FIG. 2, the elongate member 34 can be received within the outer sheath 36 such that the outer sheath 36 substantially encompasses the elongate member 34. The outer sheath 36 can be made out of any suitable material, such as a polyester, having a wall thickness of 0.0005". In some exemplary embodiments, the outer sheath 36 can act as a barrier such that the patient 30 is protected from the coil 24 and/or other components of the stylet 18.

In addition, the stylet 18 can include a reinforcement member 38 shown in detail in FIGS. 2 and 3. In some exemplary embodiments, the reinforcement member 38 is elongate so as to include a first end 40 and a second end 42. Also, the reinforcement member 38 can be made out of a material that is more rigid than the elongate member 34 and outer sheath 36, such that the reinforcement member 38 can substantially reinforce the stylet 18. However, in some exemplary embodiments, the reinforcement member 38 can allow for some degree of flexibility such that the stylet 18 can be routed along a non-linear path. In addition, because of the relative rigidity of the reinforcement member 38, the reinforcement member 38 transfers axial forces, torque forces, and other suitable forces such that a medical professional can apply force at the second end 22 (e.g., forces directed linearly along the axis X and/or rotationally about the axis X), and those forces are effectively transferred toward the first end 20 to enable intended routing of the stylet 18.

The reinforcement member 38 can be made out of any suitable material, such as a magnetic and electrically conductive material. In some exemplary embodiments, for instance, the reinforcement member 38 can be made out of 430 stainless steel.

As shown in FIGS. 2 and 3, the reinforcement member 38 can be received within the flexible elongate member 34 so as to be operatively secured therein. As such, the flexible elongate member 34 is disposed between the coil 24 and the reinforcement member 38. The reinforcement member 38 can be of substantially the same length as or longer than the elongate member 34 so as to substantially fill the channel 17 and extend between the first and second ends 20, 22 of the stylet 18. Moreover, the reinforcement member 38 is received and disposed within the coil 24 as shown in FIGS. 2 and 3. It will be appreciated that because the reinforcement member 38 can be made out of a magnetic material and is disposed within the coil 24, the reinforcement member 38 can increase the signal-to-noise ratio when current is induced in the coil 24 as described above. As such, the location of the stylet 18 can be detected with increased accuracy.

Moreover, the reinforcement member 38 can provide electrical communication between the coil 24 and the locating device 25. For instance, in some exemplary embodiments, the leads 37, 39 of the coil 24 extend through an aperture 43 (FIG. 2) of the elongate member 34, and the leads 37, 39 are electrically connected to the reinforcement member 38. Also, in some exemplary embodiments, the leads 37, 39 are secured to the reinforcement member 38 with an adhesive 45 (FIG. 2). It will be appreciated that the leads 37, 39 could be secured to the reinforcement member 38 by any suitable means, for instance, spot welding, etc. In addition, in some exemplary embodiments, an electrical connector 44 (FIG. 2) electrically connects the second end 22 of the reinforcement member 38 to the locating device 25. For instance, in some exemplary embodiments, the elongate member 34 and outer sheath 36 cooperate to define an aperture 47 extending therethrough, and the electrical connector 44 extends through the aperture 47 to electrically connect to the second end 42 of the reinforcement member 38. Also, the electrical connector 44 is electrically connected to the locating device 25. In some exemplary embodiments, the electrical connector 44 is a flexible printed circuit board. Thus, current induced in the coil 24 can be transferred via the leads 37, 39, through the reinforcement member 38, and through the electrical connector 44, to the locating device 25.

Accordingly, the reinforcement member 38 improves the signal-to-noise ratio during operation of the image guided system 10 such that the stylet 18 can be located with greater accuracy. Furthermore, the reinforcement member 38 provides adequate reinforcement for the stylet 18 such that forces can be transferred from the second end 22 of the stylet 18 to the first end 20 of the stylet 18 to allow a medical professional to more easily route the stylet 18 along a non-linear path, such as through a blood vessel. However, the stylet 18 can be flexible enough to allow the stylet 18 to bend as it is routed along the non-linear path. Thus, the stylet 18 can be located with greater accuracy and can be routed more easily by medical professionals.

Referring now to FIG. 3, the reinforcement member 38 will be discussed in greater detail. In some exemplary embodiments, the reinforcement member 38 can include a first member 46 and a second member 48. Each of the members 46, 48 are elongate and extend along the axis X. In some exemplary embodiments, the members 46, 48 have a substantially D-shaped cross-section. As such, the members 46, 48 each include a flat surface 50a, 50b, respectively. The members 46, 48 are disposed substantially symmetrically on opposite sides of the axis X such that the flat surfaces 50a, 50b oppose each other. Also, the member 46, 48 are electrically insulated from each other. For instance, in the exemplary embodiment represented in FIG. 3, a partition wall 52 is disposed between the members 46, 48. In some exemplary embodiment, the partition wall 52 is integrally connected to the elongate member 34. More specifically, in some exemplary embodiments, the elongate member 34 is made using an extrusion method such that the partition wall 52 is created.

The lead 37 of the coil 24 can be connected to the first member 46, and the lead 39 of the coil 24 can be electrically connected to the second member 48. Accordingly, the first and second members 46, 48 can have opposite polarities for proper transmission of the current of the coil 24.

Figure 4:
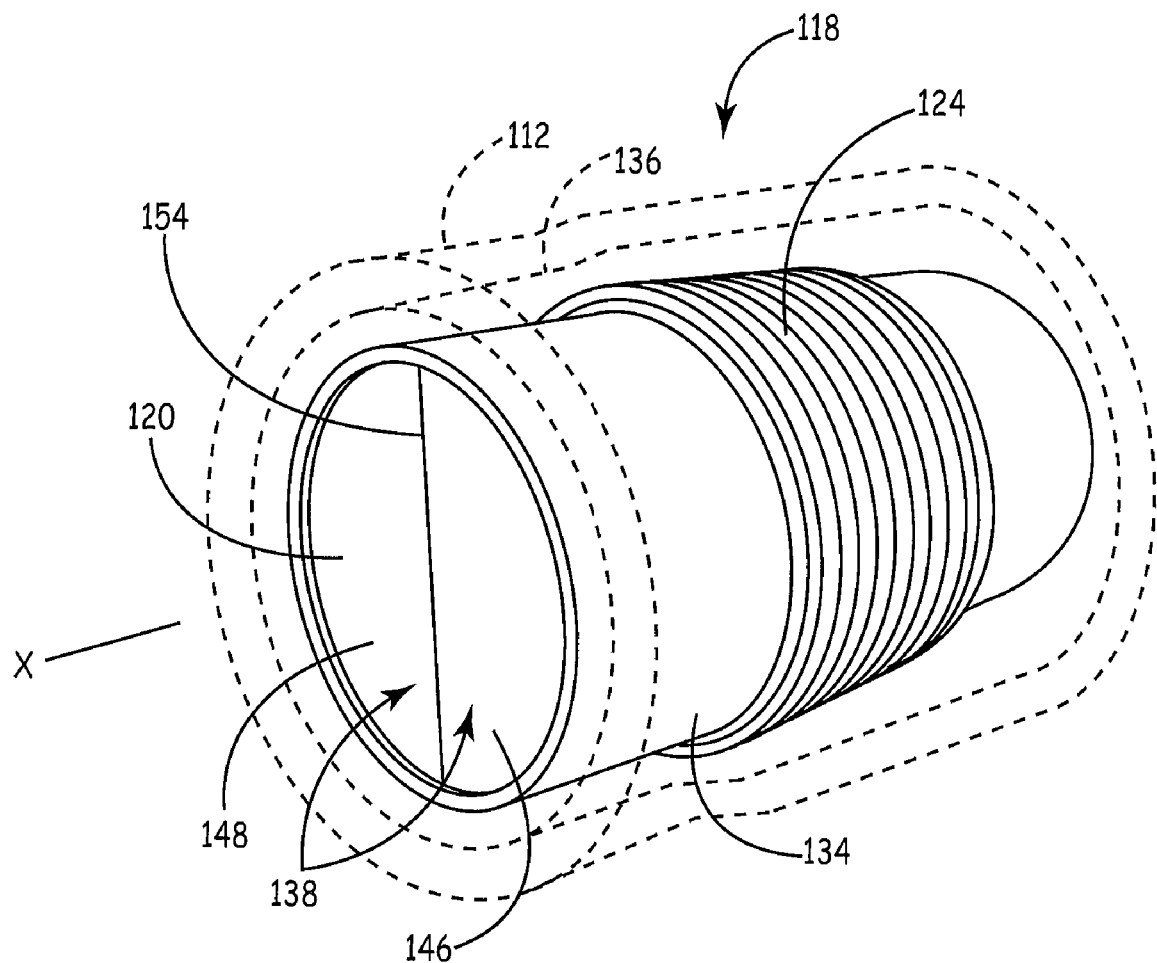
FIG. 4 is a perspective view of a stylet according to another exemplary embodiment.

Referring now to FIG. 4, another exemplary embodiment of the stylet 118 is illustrated. Components that are similar to those of the exemplary embodiment of FIG. 3 are indicated by similar reference numerals increased by 100.

As shown in the exemplary embodiment of FIG. 4, the first and second members 146, 148 of the reinforcement member 138 are electrically insulated from each other by an electrically insulating coating 154 provided therebetween. The coating 154 can be made out of any suitable material, such as parylene. Thus, the coating 154 can provide a convenient means for electrically insulating the first and second members 146, 148.

Figure 5:
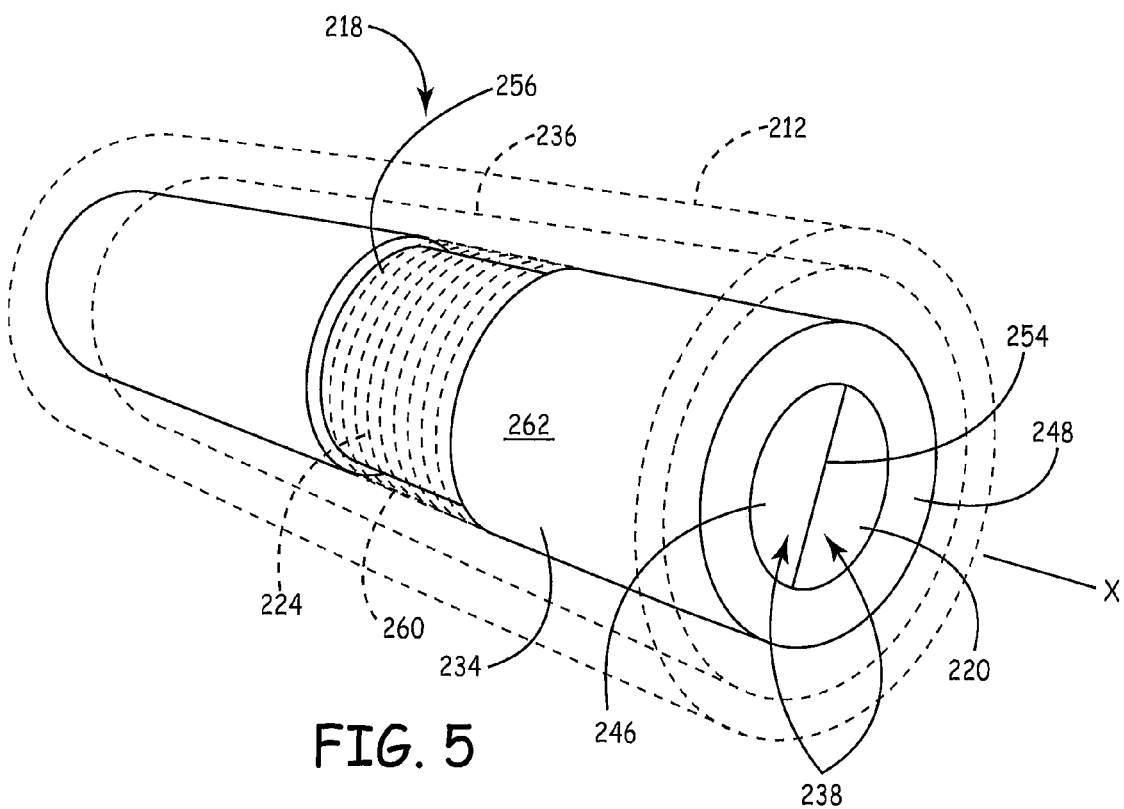
FIG. 5 is a perspective view of a stylet according to still another exemplary embodiment.

Referring now to FIG. 5, another exemplary embodiment of the stylet 218 is illustrated. It will be appreciated that components similar to those of the exemplary embodiments of FIG. 3 are indicated by similar reference numerals increased by 200.

In the exemplary embodiment shown, a recess 256 is defined within the elongate member 234 and/or the reinforcement member 248. In some exemplary embodiments, the recess 256 is tubular, extending radially inward toward and circumferentially about the axis X, and the length of the recess 256 along the axis X is approximately equal to the longitudinal length of the coil 224. As shown, the coil 224 is disposed within the recess 256. In some exemplary embodiments, the recess 256 is deep enough such that an outer surface 260 of the coil 224 is substantially flush with an outer surface 262 of the elongate member 234. As such, the coil 224 can include a substantial number of turns around the stylet 218, and yet the recess 256 allows the coil 224 to have a relatively low profile. As such, the stylet 218 can have a high signal-to-noise ratio and yet still have a relatively low profile (i.e., width).

Other exemplary embodiments of the stylet 18, 118, 218 are also envisioned. For instance, as described above, the stylet 18, 118, 218 could include a plurality of coils 24, 124, 224. Also, each coil 24, 124, 224 could include corresponding pairs of reinforcement members 38, 138, 238, which electrically connect the respective coil 24, 124, 224 to the locating device 25. Each of the reinforcement members 38, 138, 238 could extend longitudinally along the stylet 18, 118, 218 and be electrically insulated from each other in any of the ways discussed herein. Specifically, in an exemplary embodiment with two coils 24, 124, 224, there could be four reinforcement members 38, 138, 238 disposed symmetrically about the axis X. The reinforcement members 38, 138, 238 could have a wedge-shaped or substantially triangular cross section and be disposed in separate quadrants when viewed in cross section. Two of the reinforcement members 38, 138, 238 could have opposite polarities and be electrically connected to one of the coils 24, 124, 224, and the other pair of reinforcement members 38, 138, 238 could have opposite polarities and be electrically connected to the other coil 24, 124, 224.

Thus, during operation, the stylet 18, 118, 218 can be operatively coupled to the medical device 12 and inserted into a prepared incision in the patient 30. Then, the field generator 26 can generate the electromagnetic field as described above, which induces a current in the coil 24, 124, 224. The induced current is transmitted to the locating device 25 via the reinforcement member 48, 148, 248. Accordingly, the locating device 25 uses this data to accurately locate the stylet 18, 118, 218, and thus the medical device 12. Therefore, the medical professional can position the stylet 18 and the medical device 12 with a high degree of accuracy. Once in the intended position, the stylet 18 can be withdrawn from the medical device 12.

It will be appreciated that the stylet 18, 118, 218 provides substantially accurate information for the position of the medical device 12. The reinforcement member 48, 148, 248 improves the signal-to-noise ratio during use because it is made of magnetic material and because it is located within the coil 24, 124, 224. Also, the stylet 18, 118, 218 is flexible enough to be routed along a non-linear path, and yet provides enough rigidity to transfer forces between the first and second ends 20, 22 for easier routing. Furthermore, the coil 24, 124, 224 can include a relatively large number of turns without significantly increasing the profile (i.e., width) of the stylet 18, 118, 218. Thus, the stylet 18, 118, 218 can be useful in a large number of procedures, including cardiac procedures. Additionally, the stylet 18, 118, 218 can be easily withdrawn from the patient 30 without having to cut the coil 24, 124, 224, thereby reducing the risk of exposing the patient 30 to harmful materials.

The foregoing description of the exemplary embodiments has been provided for purposes of illustration and description. It is not intended to be exhaustive or to limit the invention. Individual elements or features of a particular exemplary embodiment are generally not limited to that particular exemplary embodiment, but, where applicable, are interchangeable and can be used in a selected exemplary embodiment, even if not specifically shown or described. The same may also be varied in many ways. Such variations are not to be regarded as a departure from the invention, and all such modifications are intended to be included within the scope of the invention.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A stylet for an image guided system, the image guided system including a locating device and operable for emitting an electromagnetic field for locating the stylet, the stylet comprising:
    a flexible elongate member;
    an electrically conductive member operatively secured over the flexible elongate member so as to encompass the flexible elongate member, the electrically conductive member including a positive lead and a negative lead; and
    a reinforcement member operatively secured to the flexible elongate member and which is disposed inside the electrically conductive member, the reinforcement member made of a magnetic material, the reinforcement member including a first member in electrical communication with the positive lead and a second member in electrical communication with the negative lead, the first member and second members being electrically insulated from each other, the first and second members being disposed in a substantially symmetric manner relative to a longitudinal axis of the flexible elongate member, the first and second members each have a substantially D-shaped cross section and each member having a flat surface, wherein the flat surfaces of the first and second members substantially oppose each other on opposite sides of the longitudinal axis, the reinforcement member reinforcing the stylet and providing electrical communication between the electrically conductive member and the locating device such that current induced in the electrically conductive member due to the electromagnetic field is transmitted to the locating device via the reinforcement member.

2. The stylet of claim 1, wherein the electrically conductive member is a coil.

3. The stylet of claim 1, wherein the flexible elongate member includes a partition wall disposed between the first and second members.

4. The stylet of claim 1, further comprising an electrically insulating coating provided between the first and second members.

5. The stylet of claim 1, wherein at least one of the flexible elongate member and the reinforcement member defines a recess, and the electrically conductive member is disposed within the recess.

6. The stylet of claim 1, wherein the electrically conductive member includes a plurality of helical layers.

7. The stylet of claim 1, wherein the flexible elongate member includes an aperture through which a lead of the electrically conductive member extends to electrically connect to the reinforcement member.

8. The stylet of claim 7, further comprising an adhesive that operatively secures the lead to the flexible elongate member.

9. The stylet of claim 1, wherein the flexible elongate member is disposed between the electrically conductive member and the reinforcement member.

10. The stylet of claim 1, further comprising an outer sheath that substantially encompasses the electrically conductive member, the flexible elongate member, and the reinforcement member.

11. The stylet of claim 1, wherein the electrically conductive member is disposed adjacent a first end of the flexible elongate member, and further comprising an electrical connector disposed adjacent a second end of the flexible elongate member, and wherein the reinforcement member extends generally between the first and second end of the flexible elongate member.

12. The stylet of claim 1, wherein the flexible tube, the electrically conductive member, and the reinforcement member are operable to be removably secured to a pacemaker lead.

13. A method for positioning a medical device comprising:
    electrically connecting an electrically conductive member of a stylet according to claim 1 to a locating device via a reinforcement member, the reinforcement member being made of a magnetic material and which is disposed inside the electrically conductive member;
    emitting an electromagnetic field relative to the stylet to induce a current in the electrically conductive member;
    detecting the current in the electrically conductive member with the locating device to locate the stylet; and
    positioning the medical device relative to the stylet.

14. The method of claim 13, further comprising removing the stylet from the medical device after positioning the medical device.

15. The method of claim 13, further comprising varying the electromagnetic field.

16. An image guided system comprising:
    a locating device;
    a field generator operable for emitting an oscillating electromagnetic field;
    a medical device defining a channel therein; and
    a stylet according to claim 1.

* * * * *